(12) United States Patent
Durbin et al.

(10) Patent No.: US 7,494,338 B2
(45) Date of Patent: Feb. 24, 2009

(54) 3D DENTAL SCANNER

(76) Inventors: Duane Durbin, 7660 Norcanyon Way, San Diego, CA (US) 92126; Dennis Durbin, 711 Marsolan Ave., Solana Beach, CA (US) 92075; Arun Dalmia, 149 Donnybrook Ct. NE., Ada, MI (US) 49301; Ed Childers, 3504 Oak Glen La., San Diego, CA (US) 92117

(*) Notice: Subject to any disclaimer, the term of this patent is extended or adjusted under 35 U.S.C. 154(b) by 612 days.

(21) Appl. No.: 11/032,851

(22) Filed: Jan. 11, 2005

(65) Prior Publication Data

US 2006/0154198 A1    Jul. 13, 2006

(51) Int. Cl.
*A61C 1/00* (2006.01)
*A61C 19/04* (2006.01)

(52) U.S. Cl. .......................... 433/29; 433/72

(58) Field of Classification Search .......... 433/29, 433/72, 75, 76; 600/589, 590; 33/503
See application file for complete search history.

(56) References Cited

U.S. PATENT DOCUMENTS

| | | | |
|---|---|---|---|
| 3,706,851 A * | 12/1972 | Froehlich et al. | 348/28 |
| 4,182,312 A * | 1/1980 | Mushabac | 433/68 |
| 4,575,805 A | 3/1986 | Moermann et al. | |
| 4,837,732 A | 6/1989 | Brandestine et al. | |
| 4,997,369 A * | 3/1991 | Shafir | 433/72 |
| 5,027,281 A | 6/1991 | Rekow et al. | |
| 5,343,391 A * | 8/1994 | Mushabac | 433/76 |
| 5,372,502 A | 12/1994 | Massen et al. | |
| 5,431,562 A | 7/1995 | Andreiko et al. | |
| 5,562,448 A * | 10/1996 | Mushabac | 433/215 |
| 6,243,439 B1 * | 6/2001 | Arai et al. | 378/20 |
| 6,592,371 B2 | 7/2003 | Durbin et al. | |
| 6,648,640 B2 | 11/2003 | Rubbert et al. | |
| 6,668,466 B1 * | 12/2003 | Bieg et al. | 33/503 |
| 6,885,464 B1 * | 4/2005 | Pfeiffer et al. | 356/602 |
| 2002/0028418 A1 * | 3/2002 | Farag et al. | 433/29 |

FOREIGN PATENT DOCUMENTS

WO    WO 98/48242    4/1997

* cited by examiner

*Primary Examiner*—John J Wilson

(57) ABSTRACT

Systems and methods for optically imaging a dental structure within an oral cavity by moving one or more image apertures on an arm coupled to a fixed coordinate reference frame external to the oral cavity; determining the position of the one or more image apertures using the fixed external coordinate reference frame; capturing one or more images of the dental structure through one or more of the image apertures; and generating a 3D model of the dental structure based on the captured images.

19 Claims, 10 Drawing Sheets

3D DENTAL SCANNER

BACKGROUND

The present invention relates to generating a three dimensional (3D) surface model of arbitrarily shaped objects such as dental structures.

Scanners are devices for capturing and recording information from the surface of an object. The use of scanners to determine the surface contour of objects by non-contact optical methods has become increasingly important in many applications including the in vivo scanning of dental structures to create a 3D model. Typically, the 3D surface contour is formed from a cloud of points where the relative position of each point in the cloud represents an estimated position of the scanned object's surface at the given point.

One basic measurement principle behind collecting point position data for these optical methods is triangulation. In triangulation, given one or more triangles with the baseline of each triangle composed of two optical centers and the vertex of each triangle being a target object surface, the range from the target object surface to the optical centers can be determined based on the optical center separation and the angle from the optical centers to the target object surface. If one knows the coordinate position of the optical centers in a given coordinate reference frame, such as for example a Cartesian X,Y,Z reference frame, than the relative X, Y, Z coordinate position of the point on the target surface can be computed in the same reference frame.

Triangulation methods can be divided into passive triangulation and active triangulation. Passive triangulation (also known as stereo analysis) typically utilizes ambient light and the optical centers along the baseline of the triangle are cameras. In contrast, active triangulation typically uses a single camera as one optical center of the triangle along the baseline and, in place of a second camera at the other optical center, active triangulation uses a source of controlled illumination (also known as structured light).

Stereo analysis is based upon identifying surface features in one camera image frame that are also observed in one or more image frames taken at different camera view positions with respect to the target surface. The relative positions of the identified features within each image frame are dependent on the range of each of the surface features from the camera. By observing the surface from two or more camera positions the relative position of the surface features may be computed.

Stereo analysis while conceptually simple is not widely used because of the difficulty in obtaining correspondence between features observed in multiple camera images. The surface contour of objects with well-defined edges and corners, such as blocks, may be rather easy to measure using stereo analysis, but objects with smoothly varying surfaces, such as skin or tooth surfaces, with few easily identifiable points to key on, present a significant challenge for the stereo analysis approach.

To address this challenge, fixed fiducials or a formed pattern such as dots may be placed on a target object's surface in order to provide readily identifiable points for stereo analysis correspondence. WO 98/48242 entitled METHOD AND DEVICE FOR MEASURING THREE-DIMENSIONAL SHAPES by Hans Ahlen, et. al., the content of which is incorporated by reference, discloses a method for measuring the shape of an object by first applying a pattern of paint to the object's surface and then observing the object from a multitude of positions. The pattern of paint is used in conjunction with the multiple images to perform a stereo analysis to calculate the shape of the target object's surface.

Active triangulation, or structured light methods, overcomes the stereo correspondence issue by projecting known patterns of light onto an object to measure its shape. The simplest structured light pattern is simply a spot of light, typically produced by a laser. The geometry of the setup between the light projector and the position of the camera observing the spot of light reflected from the target object's surface enables the calculation of the relative range of the point on which the light spot falls by trigonometry. Other light projection patterns such as a stripe or two-dimensional patterns such as a grid of light dots can be used to decrease the required time to capture the images of the target surface.

The measurement resolution of the target objects' surface features using structured lighting methods is a direct function of the fineness of the light pattern used and the resolution of the camera used to observe the reflected light. The overall accuracy of a 3D laser triangulation scanning system is based primarily upon its ability to meet two objectives: 1) accurately measure the center of the illumination light reflected from the target surface and 2) accurately measure the position of the illumination source and the camera at each of the positions used by the scanner to acquire an image.

To achieve the second objective, commercial 3D scanners typically utilize precision linear or rotational stages to accurately reposition either the illuminator/camera pair or the target object between image acquisitions. However, a variety of real-world situations such as 3D imaging of intra oral human teeth do not lend themselves to the use of conventional linear or rotational stages. Further, the great range in sizes and shapes of the human jaw and dentition make the use of a single fixed path system impractical.

Commercially available 3D scanner systems have been developed for the dental market that accommodate the variety of human dentition by incorporating an operator held, wand type scanner. In these systems, the operator moves the scanner over the area to be scanned and collects a series of image frames. In this case however, there is no known positional correspondence between image frames because each frame is taken from an unknown coordinate position that is dependent upon the position and orientation of the wand at the instance the frame was taken. These handheld systems must therefore rely on scene registration or the application of an accurate set of fiducials over the area to be scanned. For example, U.S. Pat. No. 6,648,640 entitled INTERACTIVE ORTHODONTIC CARE SYSTEM BASED ON INTRA-ORAL SCANNING OF TEETH by Rudger Rubbert et. al., the content of which is incorporated by reference, discloses a scanner which acquires images of the denture which are converted to three-dimensional frames of data. Pattern recognition can then be used to register the data from several frames to each other to provide a three-dimensional model of the teeth.

For 3D structures such as teeth, the use of pattern recognition or fiducials for frame registration is not optimal since tooth surfaces do not always provide sufficient registration features to allow high accuracy scene registration and accurate placement of fiducials to the required resolution is impractical over anything but the smallest tooth. U.S. Pat. No. 4,837,732 entitled METHOD AND APPARATUS FOR THE THREE-DIMENSIONAL REGISTRATION AND DISPLAY OF PREPARED TEETH and U.S. Pat. No. 4,575,805 entitled METHOD AND APPARATUS FOR THE FABRICATION OF CUSTOM-SHAPED IMPLANTS, both by Brandestini and Moermann, and whose contents are incorporated by reference, disclose a scanning system for in vivo, non-contact scanning of teeth and a method for optically mapping a prepared tooth with a non-contact scan-head. The non-contact scanner includes a light emitting diode which is used in conjunction with a plurality of slits to form a structured light pattern on a tooth's surface. The reflected light is recorded by a linear charge coupled device sensor array. Triangulation is used to map the surface contour of the scanned teeth.

U.S. Pat. No. 5,372,502 entitled OPTICAL PROBE AND METHOD FOR THE THREE-DIMENSIONAL SURVEYING OF TEETH by Massen et al., the content of which is incorporated by reference, discloses an optical based scanner for measuring the surface contour of teeth that has a similar principle of operation. As noted in the Massen et al. patent, the Biandestini et al. technique is difficult to use when there are large variations in surface topography since such large variations in the surface displace the pattern by an amount larger than the phase constant of the pattern, making it difficult to reconstruct the pattern of lines. Furthermore, precise knowledge of the angle of incidence and angle of reflection, and the separation distance between the light source and the detector, are needed to make accurate determinations of depth. Furthermore, the scanner has to be rather carefully positioned with respect to the tooth and would be unable to make a complete model of a jaw's dental structure.

U.S. Pat. No. 5,027,281 entitled METHOD AND APPARATUS FOR SCANNING AND RECORDING OF COORDINATES DESCRIBING THREE DIMENSIONAL OBJECTS OF COMPLEX AND UNIQUE GEOMETRY by Rekow et. al., the content of which is incorporated by reference, discloses a scanning method using a three axis positioning head with a laser source and detector, a rotational stage and a computer controller. The computer controller positions both the rotational stage and the positioning head. An object is placed on the rotational stage and the laser beam reflects from it. The reflected laser beam is used to measure the distance between the object and the laser source. X and Y coordinates are obtained by movement of the rotational stage or the positioning head. A three-dimensional virtual model of the object is created from the laser scanning. Thus, a plaster model of teeth can be placed on a rotational stage for purposes of acquiring shape of the teeth to form a pattern for a dental prosthesis.

U.S. Pat. No. 5,431,562 entitled METHOD AND APPARATUS FOR DESIGNING AND FORMING A CUSTOM ORTHODONTIC APPLIANCE AND FOR THE STRAIGHTENING OF TEETH THEREWITH by Andreiko et al., the content of which is incorporated by reference, describes a method of acquiring certain shape information of teeth from a plaster model of the teeth. The plaster model is placed on a table and a picture is taken of the model's teeth using a video camera positioned a known distance away from the model, looking directly down on the model. The image is displayed on an input computer and a positioning grid is placed over the image of the model teeth. The operator manually inputs X and Y coordinate information of selected points on the model teeth, such as the mesial and distal contact points of the teeth. An alternative embodiment is described in which a laser directs a laser beam onto a model of the teeth and the reflected beam is detected by a sensor. Neither technique achieves in vivo scanning of teeth.

Systems and methods have been developed that allow in vivo scanning of teeth while avoiding the need to perform pattern recognition or use fiducials for image frame registration. In these systems the accurate surface contour of a scanned object is computed from a series of active triangulation image capture frames where each frame is obtained from precisely known positions of the image aperture. U.S. Pat. No. 6,592,371 entitled METHOD AND SYSTEM FOR IMAGING AND MODELING A THREE DIMENSIONAL STRUCTURE by Durbin, et. al., the content of which is incorporated by reference, discloses a method for optically imaging the dental structure using one or more image apertures movably coupled to an intra-oral track in a manner that results in each captured image frame being obtained from a known position with respect to all other captured images. By gathering each image frame through an image aperture that is at a known position and orientation as the aperture traverses along an intra oral track this method allows the 3D surface contour of the teeth and jaw dentia to be directly computed without performing frame registration.

The intra oral cavity represents a significant challenge for accurate in vivo 3D imaging of the surface of teeth and tissue. The ability to accurately measure the center of a scanning line is affected by the translucency of teeth, the variety of other reflecting surfaces (amalgam fillings, metal crowns, gum tissue, etc.) and the obscuration due to adjacent surfaces. Further, linear or rotational motion adds to error accumulation and the variation in size and curvature of human jaws makes a "one size fits all" scanner problematic.

SUMMARY

Systems and methods for optically imaging a dental structure within an oral cavity by moving one or more image apertures on an arm coupled to a fixed coordinate reference frame external to the oral cavity; determining the position of the one or more image apertures using the fixed coordinate reference frame; capturing one or more images of the dental structure through one or more of the image apertures; and generating a 3D model of the dental structure based on the captured images.

In another aspect, a method for optically imaging a dental structure within an oral cavity by capturing one or more images of the dental structure through at least one image aperture, the image aperture movably coupled via an arm to a mobile platform that is external to the oral cavity; the trajectory of the image aperture during the image capture scan generally following a path and orientation previously generated by the user during a pre-scan trace along the dental structure surface being imaged; and generating a 3D model of the dental structure based on the images captured through the image aperture during the image capturing scan along the previously traced path.

Implementations of the above method may include one or more of the following. Via coupling with a holding arm extending into the oral cavity, the scanner head probe that houses the image aperture may be moved incrementally or continuously within the oral cavity. One or more illuminator apertures may be mounted within the scanner head probe to illuminate the dental structure. The illuminator aperture or apertures can be moved incrementally or continuously within the oral cavity. The intra-oral position and orientation of the image aperture and illuminator aperture within the intra-oral cavity may be determined by measuring the external end of the probe's holding arm position and orientation with respect to a fixed coordinate reference frame. The fixed coordinate reference frame may be defined by a coordinate reference frame reference plate (referred to herein as the reference plate) that is partially or entirely external to the oral cavity.

The reference plate may provide physical support and positioning fiducials for a mobile scanner platform that the external end of the arm holding the intra-oral image aperture and illuminator aperture is attached to. A bite fixture may be coupled to the reference plate to stabilize the jaws with respect to the reference plate's coordinate reference frame during the image capture scan. The mobile scanner platform may be a self-propelled vehicle from which the scanner head probe that houses the image aperture and illuminator aperture is extended via the holding arm into the oral cavity. The scanner head probe may rotate about the axis of the holding arm to track the angular orientation of the teeth and may be rotated more than plus or minus 180 degrees to image either the maxillary or mandibular teeth. During the image capture scan, the mobile scanner platform to which the external end of the scanner head holding arm is attached, may autonomously travel over the reference plate, positioning the scanner head with respect to the external coordinate reference frame to known positions and orientations along the dental arch as scan images are acquired. The path followed by the scanner head probe and the orientation of the scanner head probe during the image capture scan may be a replication of the path and orientation that was established by the user when the user performed a pre-scan intra-oral trace of the scanner head probe along the dental structure of interest.

In an alternative method, the path followed by the scanner head probe and the orientation of the scanner head during the image capture scan may generally follow the intra-oral path and orientation that was previously established by the user but the image capture scan path and orientation may be adjusted to optimize the position and orientation of the image aperture and the illuminator aperture with respect to the surface of the dental structure being scanned. The adjustment of the scan path may include adjustment of the image aperture or illuminator aperture positions to align the imaged dental structure in the aperture field of view. The adjustment of the scan path may include adjustment of the image aperture position to align the imaged dental structure in the image aperture depth of field. The adjustment of the scanner head orientation may include an adjustment to the image aperture or illuminator aperture orientation with respect to the dental structure to reduce image or illumination occlusion or alter the incident angle of the illumination on the surface.

The three-dimensional model generation can include performing structured light illumination and triangulation analysis on the captured images. The method includes displaying a representation of said three-dimensional model and transmitting the three-dimensional model over a network. The three-dimensional model can be used for diagnosis and treatment of a patient.

In a second aspect, a method for optically imaging a dental structure within an oral cavity by capturing one or more images of the dental structure through at least one image aperture, the image aperture movably coupled via an arm to a mobile platform that is external to the oral cavity; the trajectory of the image aperture during the image capture scan following a path and orientation generated directly by the user along the dental structure surface being imaged; and generating a three-dimensional model of the dental structure based on the images captured through the image aperture during the image capturing scan along the operator directed trajectory.

Implementations of the above method may include one or more of the following. Via coupling with a holding arm extending into the oral cavity, the scanner head probe that houses the image aperture and illuminator aperture may be moved by the operator incrementally or continuously within the oral cavity. The intra-oral position and orientation of the image aperture and illuminator aperture within the intra-oral cavity may be determined by measuring the external end of the probe's holding arm position and orientation with respect to a fixed coordinate reference frame. The fixed coordinate reference frame may be defined by a coordinate reference frame reference plate that is partially or entirely external to the oral cavity. The reference plate may provide physical support and positioning fiducials for a mobile scanner platform that the external end of the arm holding the intra-oral image aperture and illuminator aperture is attached to. A bite fixture may be attached to the reference plate to stabilize the jaws with respect to the reference plate's coordinate reference frame during the image capture scan. The mobile scanner platform may be an operator movable vehicle from which the scanner head probe that houses the image aperture and illuminator aperture is extended via the holding arm into the oral cavity. The scanner head probe may be rotated by the operator about the axis of the holding arm to track the angular orientation of the teeth and may be rotated more than plus or minus 180 degrees to image either the maxillary or mandibular teeth. During the image capture scan along the operated guided trajectory, the mobile scanner platform to which the external end of the scanner head holding arm is attached, may travel over the reference plate, measuring the position and orientation of the intra-oral scanner head probe with respect to the coordinate reference frame established by the reference plate.

The three-dimensional generation can include performing structured light illumination and triangulation analysis on the captured images. The method includes displaying a representation of said three-dimensional model and transmitting the three-dimensional model over a network. The three-dimensional model can be used for diagnosis and treatment of a patient.

In a third aspect, a system optically images a dental structure within an oral cavity with a scanner head probe adapted to be inserted inside the oral cavity; at least one image aperture coupled via an arm extending out of the oral cavity to a mobile platform; the mobile platform adapted to move the intra-oral scanner head probe along a pre-established trajectory to capture one or more images of the dental structure; and an image processor coupled to the image aperture to generate a three-dimensional (3D) model of the dental structure based on the images captured by the image aperture while traversing along the scan trajectory.

Implementations of the above aspect may include one or more of the following. Via its attachment to an arm that extends into the intra-oral cavity the scanner head probe that houses the image aperture can be moved either incrementally or continuously and oriented along an intra-oral path traced by the operator. One or more illuminator apertures may be mounted within the scanner head probe to illuminate the dental structure. The illuminator aperture or apertures can be moved incrementally or continuously within the intra-oral cavity.

During an operator directed trace of the dental structure, the position and orientation of the intra-oral scanner head probe that houses the image aperture and illuminator aperture is measured with respect to the frame of reference of an external coordinate reference frame during the complete trajectory of the trace and the trajectory position and orientation information is stored. A motor can be coupled to the external end of the scanner head probe holding arm in a manner to autonomously move the image aperture incrementally or continuously within the oral cavity along a path that follows the trajectory of the stored set of trace positions and orientations. As each scan image is captured, an image processor can evaluate the scan imagery and send commands to one or more motors or actuators to make adjustments to the image aperture scan path and orientation to optimize the scan image results. The image processor can be a structured light and triangulation processor. The image processor can move the scanner head probe intra-orally along the trajectory previously traced by the operator, scan an illumination beam and perform triangulation analysis on the captured images to generate a three-dimensional model. A display can be coupled to the image processor to show a representation of said 3D model. The image processor can be coupled to a network to transmit the 3D model to a remote system. A camera can be connected to the image aperture. The camera can be intra-orally mounted or can be mounted outside of the oral cavity.

In yet another aspect, a system optically images a dental structure within an oral cavity along an intra-oral path that follows or generally follows the trajectory of a trace previously performed by the operator; a plurality of image apertures and illuminators coupled to a holding arm extending out the oral cavity with the external end of the holding arm adapted to move, position and orient the plurality of image apertures and illuminators in a known and fixed coordinate reference frame as they move along the intra-oral path and capture one or more images of the dental structure; and an image processor coupled to the image apertures to generate a three-dimensional (3D) model of the dental structure based on the images captured by the image apertures at each of their known positions and orientations.

In yet another aspect, a system optically images a dental structure within an oral cavity along an intra-oral path for which the position and orientation of the scanner head probe is measured by the system as the scanner head probe path is manipulated by the operator in a manner to scan the dental surfaces of interest; a plurality of image apertures and illuminator apertures coupled to a holding arm extending out the oral cavity with the external end of the holding arm adapted to allow the operator to move the plurality of image apertures and illuminator apertures and capture one or more images of the dental structure; a position processor that couples to the external end of the holding arm coupled to the intra-oral image apertures and illuminator apertures and measures in a fixed coordinate reference frame the position and orientation of each image and illuminator aperture during the capture of each image obtained during the image capture scan; and an image processor coupled to the image apertures to generate a three-dimensional model of the dental structure based on the images captured by the image apertures.

Advantages of the system may include one or more of the following. The system enables an operator to perform a trace along the dental structure of interest with the intra-oral scanner head probe thereby accommodating a wide range of patient jaw and dentia sizes, shapes and orientations. The system automatically provides intra-oral scanning and image capturing of the traced dental structures in the jaw through an optical aperture and combines the information available in the entire set of images obtained during the scan to create an accurate 3D model of the scanned structures. Intra-oral images of dental structures can be taken rapidly through intra-oral image apertures and with high resolution. Further, the image aperture position and orientation are known using a fixed coordinate reference frame such that the acquired images can be directly processed into accurate 3D models of the imaged dental structures.

Other advantages may include one or more of the following. The images and models can be used in dental diagnosis and used as patterns for the specification and manufacture of dental prosthetics such as bridgeworks, crowns or other precision moldings and fabrications. In addition, the system produces 3D models useful in the diagnosis and treatment planning process for dental malocclusions. The system-produced data representing a set of dental images and models can be transmitted electronically to support activity such as professional consultations or insurance provider reviews, and the images and models may be electronically archived for future reference. The digital 3D model of patient's teeth and other dental structures has advantages over a conventional physical model due to the following: 1) the 3D model is efficiently created in a single step with accuracy meeting or exceeding the conventional multiple step impression technique; 2) reduced storage costs; 3) immediate, labor-free retrieval and archiving; 4) no model breakage; 5) integrates directly into computer based analysis tools for diagnosis and treatment planning; 6) digital models backup; 7) e-mails to colleagues, dental specialists, insurance companies; 8) access to information from home, satellite office; 9) effective presentation tool; and 10) reduces staff time required for dental impressions and models.

The above and other features and advantages of the present invention will be apparent in the following detailed description of the preferred embodiments of the present invention when read in conjunction with the accompanying drawings in which corresponding parts are identified by the same reference symbol.

BRIEF DESCRIPTION OF THE DRAWINGS

To better understand the other features and technical concepts of the present systems, one may clearly read the description of the following embodiments and the accompanying drawings, in which.

DESCRIPTION

Figure 1:
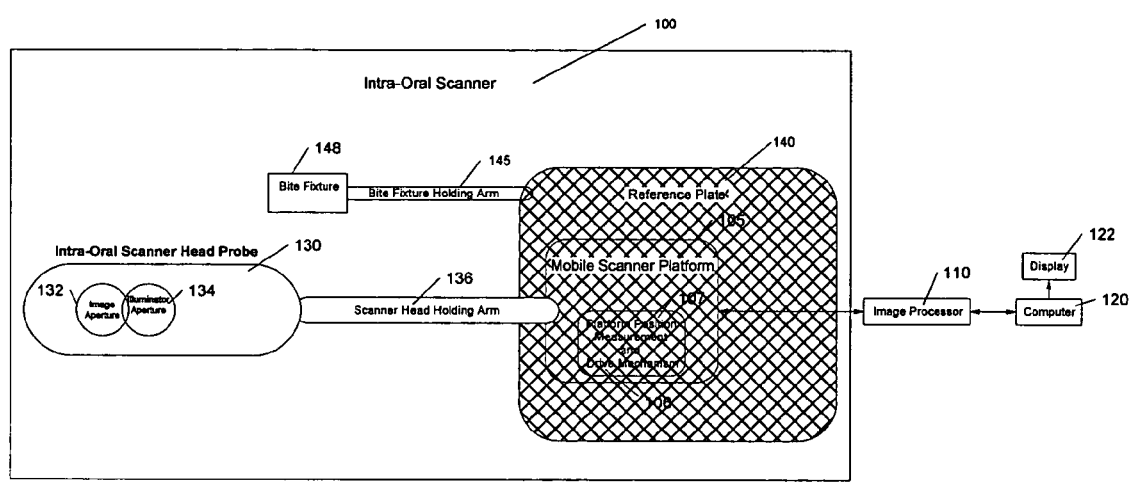
FIG. 1 illustrates an embodiment of a system for performing intra-oral scanning.
Figure 2A:
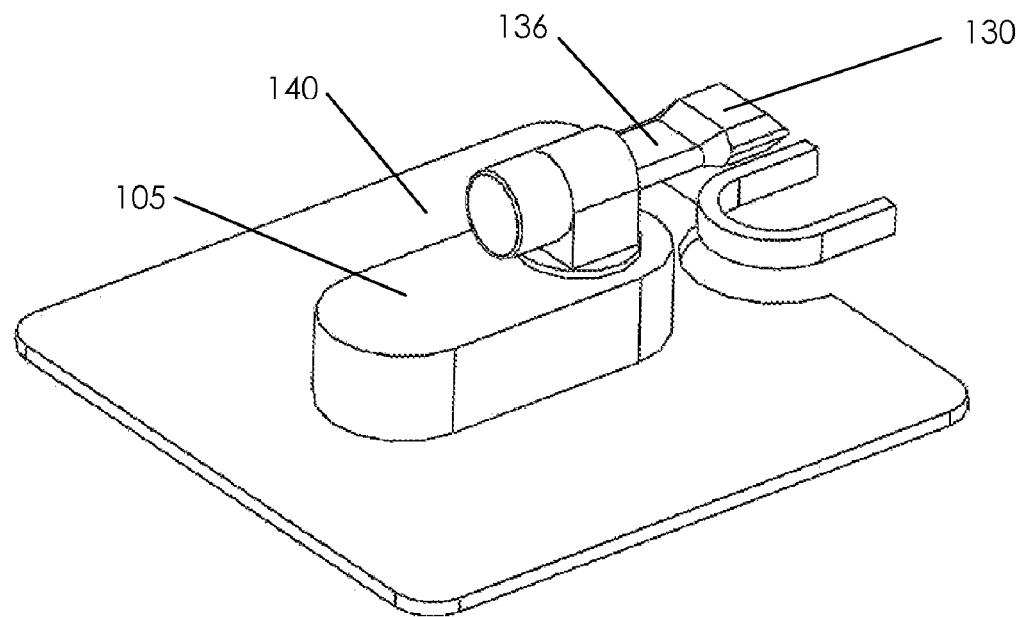
FIGS. 2A-2B show perspective views of the scanner of FIG. 1.
Figure 2B:
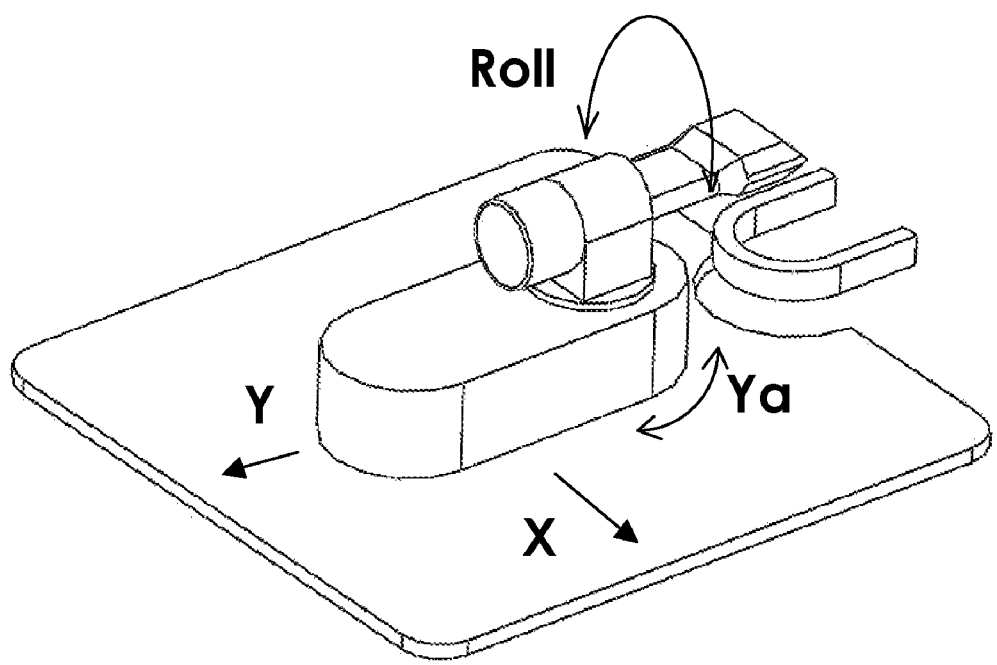
Figure 3:
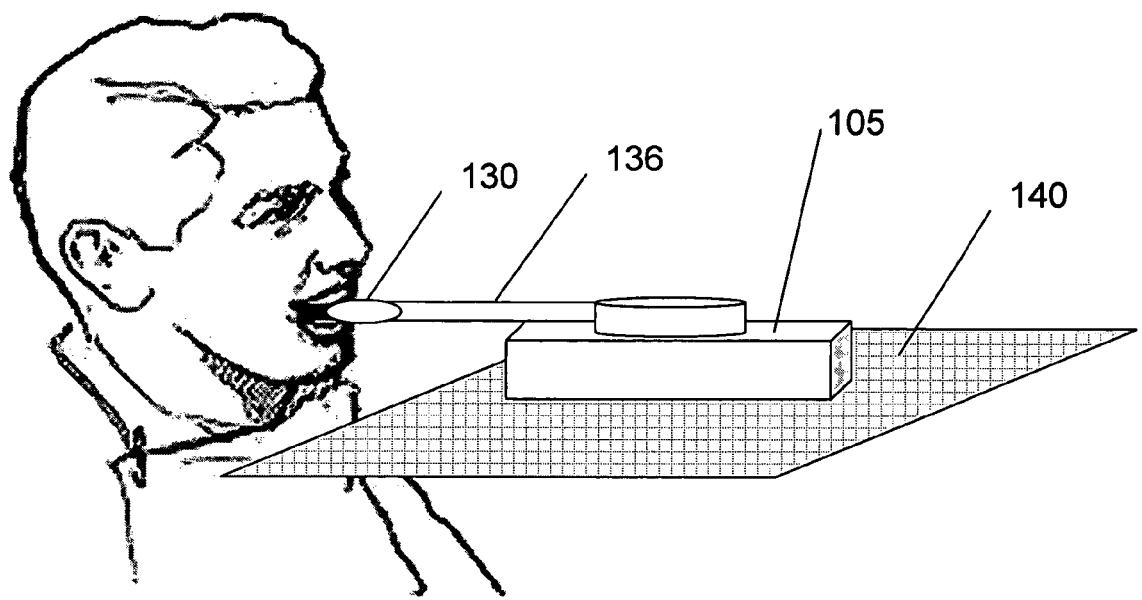
FIG. 3 shows a diagram of the scanner during an intra-oral scan.
Figure 4:
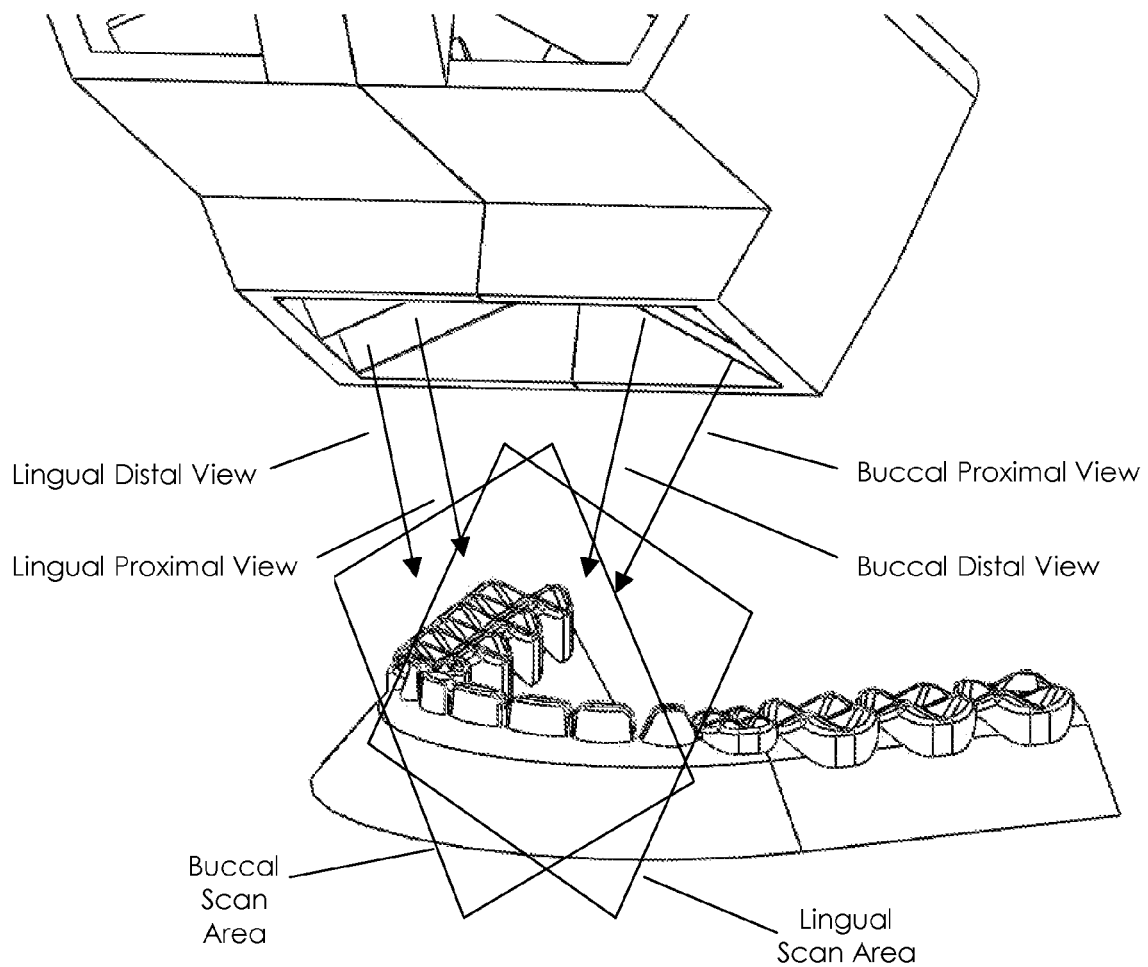
FIG. 4 illustrates a scan head with a plurality of scan views.

Referring to FIG. 1, a system block diagram depicting instrumentation used in scanning teeth and other dental structure images in vivo and in generating 3D models is shown. The intra-oral 3D imaging system of FIG. 1 uses a planar reference plate to determine the scanner head's position. This plate provides physical support and positioning fiducials for a mobile scanner platform. In one embodiment, the mobile scanner platform is a miniature, self-propelled vehicle from which the scanner head is extended via an arm into the oral cavity. The scanner platform travels over the reference plate, positioning the scanner head along the dental arch as range profiles are acquired. The scanner head rotates on the axis of the scanner head holding arm to track the angular orientation of the teeth and may be rotated 180 degrees to image either the maxillary or mandibular teeth.

In FIG. 1, an intra-oral scanner 100 utilizes an intra-oral scanner head probe 130 adapted to be placed inside the mouth of the patient (intra-oral cavity). The intra-oral scanner 100 captures images of various dental structures in the mouth and communicates this information with an image processor 110. The image processor 110 in turn can communicate with a computer 120 and can display images of the dental structures on a display 122 connected to the computer 120. Alternatively, functionalities of the computer 120 such as data storage and display can be provided directly by the image processor 110 in another embodiment. Images and 3D models derived from the images can be transmitted as digital files to other equipment or locations by the computer 120.

In one embodiment, the intra-oral scanner 100 includes a coordinate reference frame reference plate (referred to herein as the reference plate) 140. The reference plate 140 may include positioning markers or grids to assist in determining positional data. A mobile scanner platform 105 is mounted on the reference plate 140.

The mobile scanner platform 105 includes a platform position measurement mechanism 107 and a drive mechanism 106, among others. The drive mechanism 106 can incrementally or continuously move the image aperture 132 and the illuminator 134 to various positions in the intra-oral cavity. In one embodiment, the image aperture 132 and the illuminator aperture 134 are movably mounted on the intra-oral scanner head probe 130 that is driven by the drive mechanism 106. The drive mechanism 106 can be electrically actuated to move the image aperture 132 and the illuminator aperture 134 around teeth and other structures in the jaw. Any of a variety of drive motors can be used, and the power of the motor through the drive mechanism 106 can be translated into motion for the image aperture 132 and the illuminator aperture 134 through rotary, linear, hydraulic, or pneumatic mechanisms for example.

The drive mechanism 106 moves the image aperture 132 and the illuminator aperture 134 around the oral cavity and positions the image gathering aperture(s) and illuminator(s) apertures at known positions while taking images of the dental structures. The intra-oral scanner platform 105 actuates the intra-oral scanner head probe 130 through the scanner head holding arm 136. The intra-oral scanner head probe 130 includes an image aperture 132 and an illuminator aperture 134.

The image aperture 132 can capture images of the dental structures. In one embodiment, the image aperture 132 can be an objective lens followed by relay lens in the form of a gradient index lens to transmit images of the dental structures along a pre-selected distance to a camera.

The output of the image aperture 132 can be provided to one or more sensors for detecting and converting incident light—first into electronic charge (electrons) and, ultimately into digital bits. In one implementation, the output of the image aperture 132 is provided to a camera (not shown), which can be analog or digital. In one embodiment, the camera contains one or more image sensor(s) used to create digital images of the dental structure. These sensors can be devices such as a charge-coupled device (CCD) sensor or a complementary metal oxide semiconductor (CMOS) image sensor. The image sensor can be an array of individual photosensitive cells (pixels) whose size determines the limiting resolution. Image sensor arrays can have from 16×16 pixels to more than 1024×1024 pixels, and the arrays can be symmetrical or asymmetrical.

Further, a source of light delivered through the illuminator aperture 134 illuminates the dental structures in the field of view of the image aperture 132. The light can be white light, light shown in one or more colors, or can come from a laser beam. The intensity of the light source used to illuminate the dental structure is ideally controllable and is in the frequency range of visible or infra-red light. In one embodiment, the light source can be integral to the intra-oral scanner head probe 130. In another embodiment, light can be routed from the light source to the illuminator aperture 134 by one or more fiber optic cables or gradient index lenses (not shown The field of illumination may be greater than the field of view of the image aperture 132 and may range up to 180 degrees. In one embodiment, the field of illumination may be a focused beam that illuminates a line on the dental structure with an illumination line length of dimensions greater than 20 mm and an illumination line width of dimensions less than 5 mm.

The intra-oral scanner 100 can also incorporate a bite fixture 148 that is attached to the reference plate via a bite fixture holding arm 145. In preparation for a dental scan, the bite fixture 148 is placed in the intra-oral cavity in a manner that allows the patient to bite down and hold the bite fixture 148 firmly between the upper and lower jaws. The bite fixture 148 serves to keep the patient's mouth open during the dental scan and also stabilizes the position of the jaws with respect to the coordinate reference frame of the reference plate 140 during the scan. The scanner head holding arm 136 extends the reach of the intra-oral scanner head probe 130 housing the image aperture 132 into the oral cavity, enabling the intra-oral scanner head probe 130 to be moved incrementally or continuously within the oral cavity. Further, the illuminator aperture or apertures 134 can also be moved incrementally or continuously within the oral cavity. The intra-oral position and orientation of the image aperture 132 and illuminator aperture 134 within the intra-oral cavity may be determined by measuring the external end of the intra-oral scanner head probe 130's holding arm 136 position and orientation with respect to a fixed coordinate reference frame defined by the reference plate 140 that is partially or entirely external to the oral cavity.

The reference plate 140 provides physical support and positioning fiducials for a mobile scanner platform that is attached to the external end of the scanner head holding arm 132 holding the intra-oral image aperture 132 and illuminator aperture 134. The bite fixture 148 may be coupled to the reference plate 140 to stabilize the jaws during the image capture or scan. In one embodiment, the mobile scanner platform can be a self-propelled vehicle from which the intra-oral scanner head probe that houses the image aperture and illuminator aperture is extended via the scanner head holding arm into the oral cavity. The intra-oral scanner head probe may rotate about the axis of the scanner head holding arm to track the angular orientation of the teeth and may be rotated more than plus or minus 180 degrees to image either the maxillary or mandibular teeth.

To capture the three-dimensional geometry of the dentition, many profiles are acquired to create a cloud of points from which a surface may be reconstructed. It is algorithmically convenient to collect these profiles during a sweep along a continuous path of motion as this allows for straightforward interpolation of interlinear points via triangular tessellation. Each such set of profiles is termed a scan, and multiple scans may be easily combined in a single surface reconstruction if each scan's position orientation is known with respect to the same coordinate reference frame. The sweeps of the scans need not be linear or regularly sampled; and they should be continuous and densely sampled. The precision required for the motion of the intra-oral scanner head probe with respect to the dental arch need only be sufficient to avoid collision with the teeth and to keep the entire tooth cross-section in view.

In one embodiment, the dental geometry can be scanned with the intra-oral scanner head probe moving within a single plane. For this embodiment, the intra-oral scanner head probe moves in a plane at a constant offset from the surface of the reference plate. The orientation of the reference plate to the dental arch is set up manually by the operator in preparation for scanning. The mobile scanner platform's drive mechanism allows for motion in x, y, and yaw. An additional degree of freedom (roll) is provided by rotation of the intra-oral scanner head probe about the axis of the scanner head holding arm. Each of these drive mechanisms may be motorized using miniature stepper motors.

In one implementation, for position measurement, two downward-looking area cameras in the base of a turret mounted in the mobile scanner platform are used to image a grid pattern and fiducials photo-etched onto the reference plate. These two images may be combined to provide x, y and yaw angle measurements for the mobile scanner platform turret with respect to the coordinate reference frame of the reference plate. The remaining roll coordinate of the intra-oral scanner head probe may be measured using a laser, a rotating mirror and a linear array CMOS imager.

During the image capture scan, the mobile scanner platform to which the intra-oral scanner head probe 130 is attached via the scanner head holding arm 136, may autonomously travel over the reference plate 140, positioning the intra-oral scanner head probe 130 with respect to the external coordinate reference frame defined by the reference plate 140 to known positions and orientations along the dental arch as scan images are acquired. The path followed by the intra-oral scanner head probe 130 and the orientation of the intra-oral scanner head probe 130 during the image capture scan may be a replication of the path and orientation that was established by the user when the user performed a pre-scan intra-oral trace of the intra-oral scanner head probe along the dental structure of interest.

In an alternative embodiment, the path followed by the intra-oral scanner head probe 130 and the orientation of the intra-oral scanner head probe 130 during the image capture scan may generally follow the path and orientation previously established by the user but the image capture scan path and orientation may be adjusted to optimize the position and orientation of the image aperture 132 and the illuminator aperture 134 with respect to the surface of the dental structure being scanned. The adjustment of the scan path may include adjustment of the image aperture 132 or illuminator aperture 134 positions to align the imaged dental structure in the aperture field of view. The adjustment of the scan path may include adjustment of the image aperture position to align the imaged dental structure in the image aperture depth of field. The adjustment of the scanner head orientation may include an adjustment to the image aperture 132 or illuminator aperture 134 orientations with respect to the dental structure to reduce image or illumination occlusion or alter the incident angle of the illumination on the surface.

The three-dimensional model generation can include performing structured light illumination and triangulation analysis on the captured images. The system can display a representation of the three-dimensional model and transmitting the three-dimensional model over a network. The three-dimensional model can be used for diagnosis and treatment of a patient.

The system can optically image a dental structure within an oral cavity by capturing one or more images of the dental structure through at least one image aperture. During this time, the image aperture 132 is moved by the scanner head holding arm 136 connected to the mobile scanner platform 140 external to the oral cavity.

In another embodiment, the trajectory of the image aperture during the image capture scan follows a path and orientation generated directly by the user along the dental structure surface being imaged. Based on the captured images, the system generates a three-dimensional model of the dental structure based on the images captured through the image aperture during the image capturing scan along the operator directed trajectory.

For this embodiment, the scanner head holding arm 136 extending into the oral cavity, the intra-oral scanner head probe 130 that houses the image aperture 132 and illuminator aperture 134 may be moved by the operator incrementally or continuously within the oral cavity. The intra-oral position and orientation of the image aperture and illuminator aperture within the intra-oral cavity may be determined by measuring the external end of the probe's holding arm position and orientation with respect to a fixed coordinate reference frame. The fixed coordinate reference frame may be defined by a coordinate reference frame established by a reference plate 140 that is partially or entirely external to the oral cavity. The reference plate may provide physical support and positioning fiducials for the mobile scanner platform 105 that the external end of the scanner head holding arm 136 holding the intra-oral image aperture 132 and illuminator aperture 134 is attached to. A bite fixture 148 may be attached to the reference plate to stabilize the jaws during the image capture scan. The mobile scanner platform 105 may be an operator movable vehicle from which the intra-oral scanner head probe 130 that houses the image aperture and illuminator aperture is extended into the oral cavity via the scanner head holding arm. The intra-oral scanner head probe 130 may be rotated by the operator about the axis of the scanner head holding arm 136 to track the angular orientation of the teeth and may be rotated more than plus or minus 180 degrees to image either the maxillary or mandibular teeth. During the image capture scan along the operated guided trajectory, the mobile scanner platform 105 may travel over the reference plate 140, measuring the position and orientation of the intra-oral scanner head probe 130 with respect to the coordinate reference frame established by the reference plate.

The system optically images a dental structure within an oral cavity with a scanner head probe adapted to be inserted inside the oral cavity; at least one image aperture coupled via an arm extending out of the oral cavity to a mobile platform; the mobile platform adapted to move the intra-oral probe end of the attached arm along an operator directed scan trajectory to capture one or more images of the dental structure; and an image processor coupled to the image aperture to generate a three-dimensional model of the dental structure based on the images captured by the image aperture while traversing along the scan trajectory.

The operation of this 3D imaging system entails the following steps (assuming a mandibular scan for illustrative purposes):

Step 1. Preparing the patient's teeth for imaging and optionally applying a fluorescent dye coating.

Step 2. Positioning the intra-oral scanner at the opening of the patient's mouth.

Step 3. Stabilizing the patient's dental arch with respect to the reference plate using a bite fixture, cheek or chin rest as appropriate.

Step 4. Placing the system in track learning mode, inserting the intra-oral scanner head probe into the intra-oral cavity and manually moving the intra-oral scanner mobile scanner platform or the scanner head holding arm in a manner such that the intra-oral scanner head probe travels roughly above the dental arch in the region of interest for the dental scan.

Step 5. Engaging the system's scan mode and allowing it to scan back across the just-learned path at a controlled rate and with automatic adjustments for precise centering over the dental arch.

Step 6. Review the 3D model of the scanned dental structures on the system display. During an operator directed trace of the dental structure (Step 4), the position and orientation of the intra-oral scanner head probe that houses the image aperture and illuminator aperture is measured with respect to the frame of reference of an external coordinate reference frame during the complete trajectory of the trace and the trajectory position and orientation information is stored. A motor can be coupled to the external end of the scanner head holding arm in a manner to autonomously move the image aperture incrementally or continuously within the oral cavity along a path that follows the trajectory of the stored set of trace positions and orientations. As each scan image is captured, an image processor can evaluate the scan imagery and send commands to one or more motors or actuators to make adjustments to the image aperture scan path and orientation to optimize the scan image results. The image processor can be a structured light and triangulation processor. The image processor can move the scanner head probe intra-orally along the trajectory previously traced by the operator, control an illumination beam and perform triangulation analysis on the captured images to generate a three-dimensional model. A display can be coupled to the image processor to show a representation of said 3D model. The image processor can be coupled to a network to transmit the 3D model to a remote system. A camera can be connected to the image aperture. The camera can be intra-orally mounted or can be mounted outside of the oral cavity.

The system optically images a dental structure within an oral cavity along an intra-oral path that follows or generally follows the trajectory of a trace previously performed by the operator; a plurality of image apertures and illuminators coupled to a holding arm extending out the oral cavity with the external end of the holding arm adapted to move, position and orient the plurality of image apertures and illuminators in a known and fixed coordinate reference frame as they move along the intra-oral path and capture one or more images of the dental structure; and an image processor coupled to the image apertures to generate a three-dimensional model of the dental structure based on the images captured by the image apertures at each of their known positions and orientations.

The system can also optically image a dental structure within an oral cavity along an intra-oral path for which the position and orientation of the scanner head is measured by the system as the scanner head path is manipulated by the operator in a manner to scan the dental surfaces of interest; a plurality of image apertures and illuminator apertures coupled to a holding arm extending out the oral cavity with the external end of the holding arm adapted to allow the operator to move the plurality of image apertures and illuminator apertures and capture one or more images of the dental structure; a position processor that couples to the external end of the holding arm coupled to the intra-oral image apertures and illuminator apertures and measures in a fixed coordinate reference frame the position and orientation of each image and illuminator aperture during the capture of each image obtained during the image capture scan; and an image processor coupled to the image apertures to generate a three-dimensional model of the dental structure based on the images captured by the image apertures.

In one implementation, range data is acquired by imaging the profile created by the intersection of a plane of laser light with a fluorescent dye applied to the surface of the teeth from an angle offset from the laser plane. The scanner head comprises one or more ranger assemblies each of which projects a laser plane and optically combines multiple views of the surface illuminated by the laser plane. In implementations using multiple rangers, the rangers may be temporally multiplexed so that there is no confusion between their projected illumination beams. In one implementation using two rangers, each ranger's imagery is conducted via a GRIN-relay (GRadient INdex) rigid endoscope to a sensor located external to the oral cavity along with its associated electronics. This configuration allows four views of the teeth to be imaged using two sensors while minimizing the intraoral volume of the device. During a typical scan of a two ranger implementation, one ranger is buccal and the other lingual and each ranger combines both a distal and proximal view. The views are all nominally looking down (in the case of a mandibular scan) at the crown of the teeth.

In one embodiment, the 3D imaging system comprises two identically constructed rangers, one for lingual views and one for buccal views. The two rangers' image profiles are nominally in the same plane, although the laser illumination beam is projected from different directions for each ranger. Each ranger may use a set of mirrors in the scanner head to combine a proximal and distal view of the projected profile. These combined images are conducted out of the oral cavity by a GRIN-relay endoscope arrangement, which resides in the scanner head holding arm and terminates in the upper portion of the mobile scanner platform. A coupling lens, a CMOS imaging sensor and its associated electronics reside at the mobile scanner platform end of the endoscope. Also, in one embodiment, at the mobile scanner platform end of the endoscope is the laser diode that provides the source for the ranger's laser illumination beam projection optics.

Figure 5A:
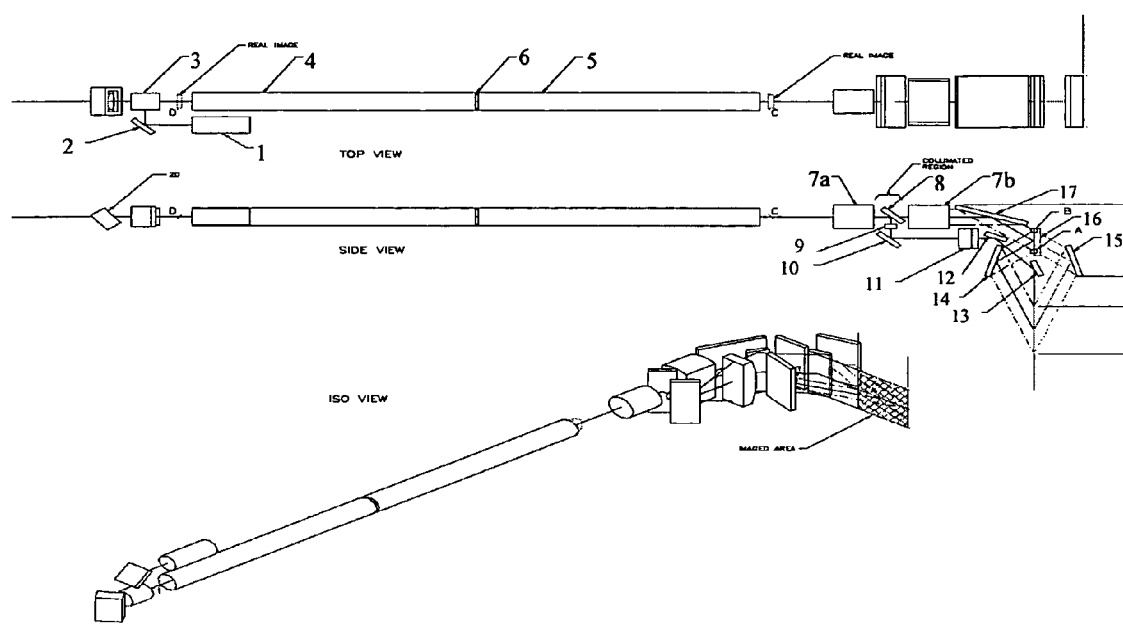
FIG. 5A shows an exploded view diagram of an exemplary ranger optical train layout.
Figure 5B:
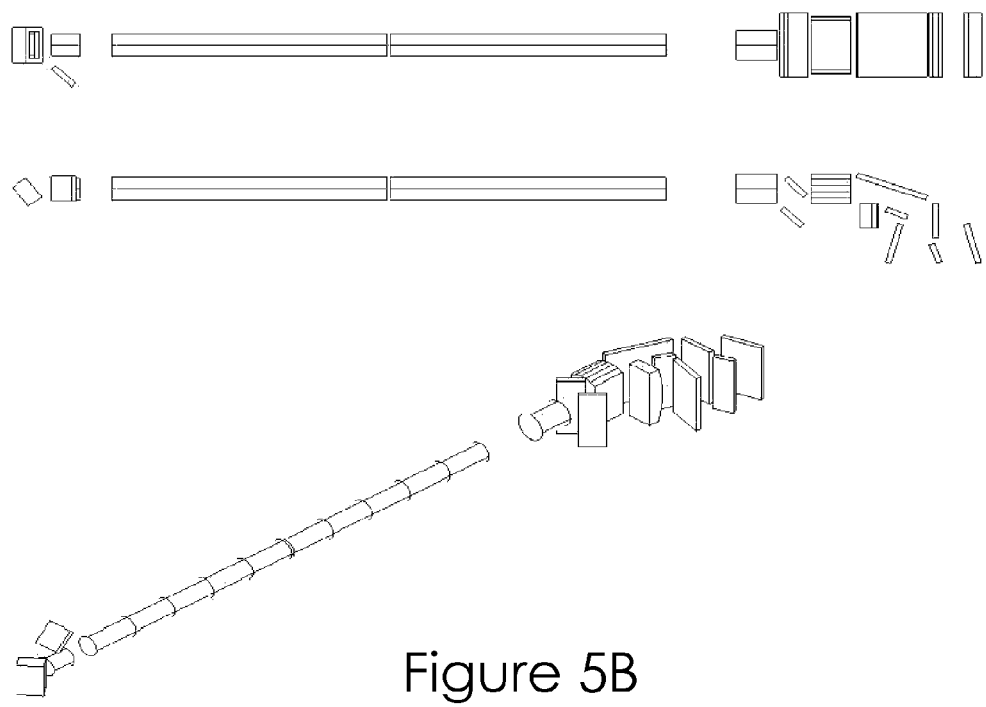
FIG. 5B shows a top view, a side view, and a perspective view of the optical train layout of FIG. 5A.
Figure 5C:
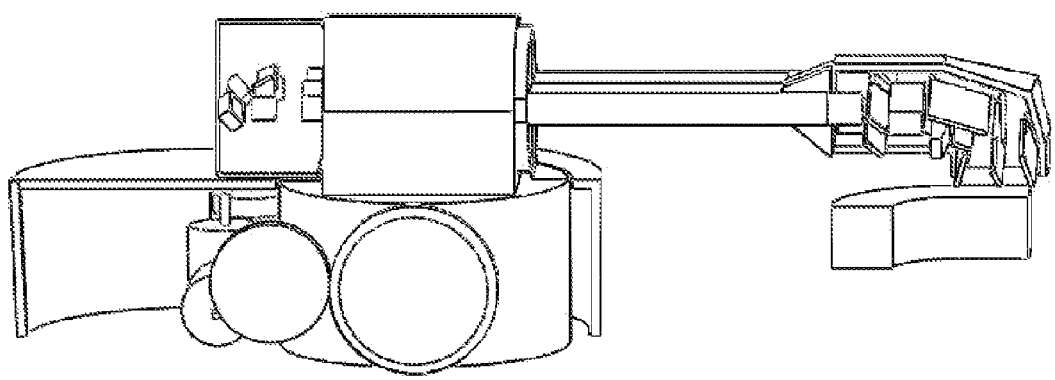
FIG. 5C shows a cross-sectional view of the optical train of FIG. 5A in a scanner head.

FIG. 5A shows an exemplary ranger optical train layout. A laser diode unit 1 includes integral collimating and focusing optics for a laser beam. The beam is folded off of mirror 2 and is further folded onto the GRIN-relay axis in optic 3 which is as multi-element unit that may include a beam combiner, low-pass filter and a coupling lens for the profile imagery. The focus of the diode unit 1 is set so that the system generates a waist at the image plane of the GRIN relay. This results in the beam emerging from the other end of the GRIN-relay with a waist at the GRIN-relay's other image plane. The GRIN relay itself may be comprised of two ¼ pitch GRIN rod lenses 4-5 that are actually slightly less then ¼ pitch in length so that the image planes are approximately 1 mm removed from the ends of the rods. These rods may be separated by an elastromeric O-ring 6 that provides an aperture stop and allows for slight thermal expansions without stressing the optics.

When the beam emerges from the GRIN-relay it passes through the first half of a macro objective 7*a* and is split out of the imaging path by a wavelength selective beam splitter 8. In this embodiment, the beam splitter is in the center of the objective so that it introduces minimal aberration in the collimated image flow. The laser beam then passes through a focusing lens 9 and is folded by a mirror 10 which has a line-generating diffraction grating etched onto it. The fan of laser light expands in one direction until it encounters a cylindrical optic 11, which ends the expansion and yields a constant width ribbon of laser light the width of the imaging area. It is then folded off of mirrors 12 and 13 to orient it in the proper imaged plane.

As alternatives to sharing the GRIN-relay as a conduit for both the laser illumination and the image return path, the system can also use fiber-coupling of the laser beam or collimating the laser beam and propagating it in free space beside the imaging relay. This would change the path between 3 and 8 and require different optics be introduced in a manner that is well known to those practiced in the art.

Next, the image combining mirror system is discussed. This system uses a set of mirrors to form an image combiner known to those skilled in the art such as optical systems that overlay two symmetrically placed views of the laser profile to create one composite profile that alleviates sensor occlusion problems encountered with a single view.

In one embodiment, symmetrically offset views are provided through separate lenses and sensors for each view and the views are digitally combined. The mirror-based combiner performs the same function in the analog domain. In doing so, it eliminates half of the imaging optics and sensors and halves downstream data bandwidth requirements.

The image combiner may include view mirrors 14 and 15 and the approximately 50% mirrored combiner 16. The image combiner operation is explained by the dash-dot and dash-dot-dot rays drawn from the far edge of and near edges of the profile image area in FIG. 5A. The far (dash-dot) ray from the left view is folded off the left view mirror 14 and encounters the partially mirrored surface of the image combiner 16 at point A. The far ray from the right view is similarly folded off the right view mirror 15 and passes through the non-reflective side of the image combiner 16 to emerge coincident with the equivalent point from the left view at point A. Similarly the rays from the near edge combine at point B. Mirror 17 redirects the combined image so that it can be viewed from the direction of the GRIN-relay imaging system.

Next the GRIN lens relay imaging system is discussed. In one implementation where the physical size of the video imagers along with the electronics mounted in very close proximity precludes their placement in the sensor head probe, an endoscopic imaging system is employed to remove the sensors and their associated electronics from the oral cavity. A number of endoscopic relay systems may be used, including: fiber optic, lens-and-rod and GRIN-relay.

The endoscopic imaging system comprises a macroscopic objective constructed of optics 7a and 7b which images the profile plane to perform a real image at an oblique angle at plane C this image is relayed by the two ¼ pitch GRIN rods to form an inverted image at plane D at the sensor end of the relay. This image is then magnified by coupling lens 3 which has an integral filter which blocks light at wavelengths outside the wavelengths of interest. For example, in one implementation, the filter may block out the laser illumination radiation and only allow the light at the wavelength of a fluorescent coating placed on the scanned surfaces to pass. This coupling lens forms an image on the sensor 20 which is oriented to produce a sharp focus throughout the imaged plane.

The two or more rangers may work in a temporally multiplexed manner, with one ranger's laser strobed and the image integrated on its sensor and then the other ranger's laser are strobed and images integrated. As the rangers collect the profiles of the scanned surfaces the entire assembly is maneuvered so that path of the sensor head probe traverses a continuous path above the dental arch.

The rangers may be mounted to the mobile sensor platform using thin section bearings that allow for rotation about the long axis of the optical arm, allowing motion in the roll axis. The mobile scanner platform itself is free to rotate and translate on the planar reference plate and in one embodiment travels on its surface via three glides. Drive wheels on the chassis of the mobile sensor platform, which engage the surface of the plate, control the translation and rotation of the platform. In one embodiment, a third drive spins a turret contained within the mobile sensor platform chassis with respect to the direction of travel of the chassis. The three degrees of freedom provided by the implementation allow the sensor head probe to traverse any path in the plane offset from the reference surface. The roll axis allows the views of the rangers to follow the angle of the dental arch. Movement in each of these axes may be driven by miniature stepper motors. The motion control may run open loop on a moment-to-moment basis, and any accumulated error can be corrected occasionally using the results of the position determination system described below.

Figure 6:
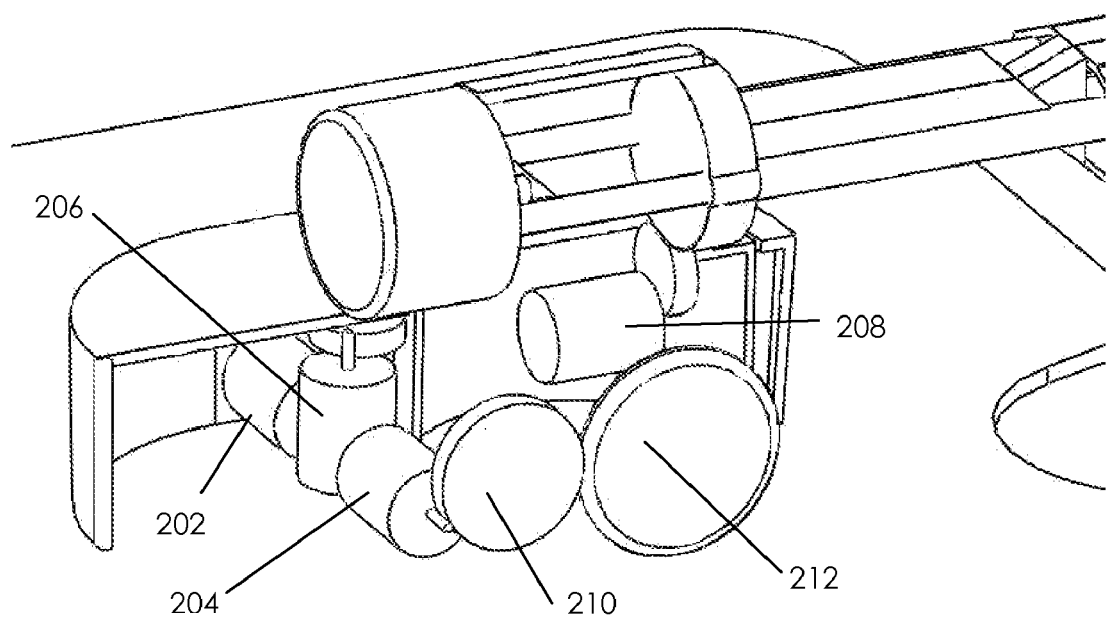
FIG. 6 shows an exemplary embodiment for actuating movements for the scanner head of FIG. 5A.

In one implementation, the roll axis, the two wheels and the rotation axis require four separate drive motors. FIG. 6 shows an implementation with all four drives using friction wheel drive arrangements with the friction wheels driven directly by the miniature stepper motor shafts. The 4-axis friction wheel drive uses left and right wheel motors 202-204. The right wheel motor 204 drives a friction wheel 210 which engages a drive wheel 212. The left wheel motor 202 operates in a similar manner. A yaw axis motor 206 and a roll axis motor 208 are provided to provide yaw and roll motion to further actuate the assembly. The motors shown are available from MicroMo, Inc.

The position of the scanner head probe 130 is determined by considering the position of the mobile scanner platform chassis on the reference plate and the angular position of the roll axis as determined by the laser/mirror/detector arrangement in the upper portion of the mobile scanner platform. The position of the mobile scanner platform on the reference plate is determined by a planar encoder system.

Figure 7:
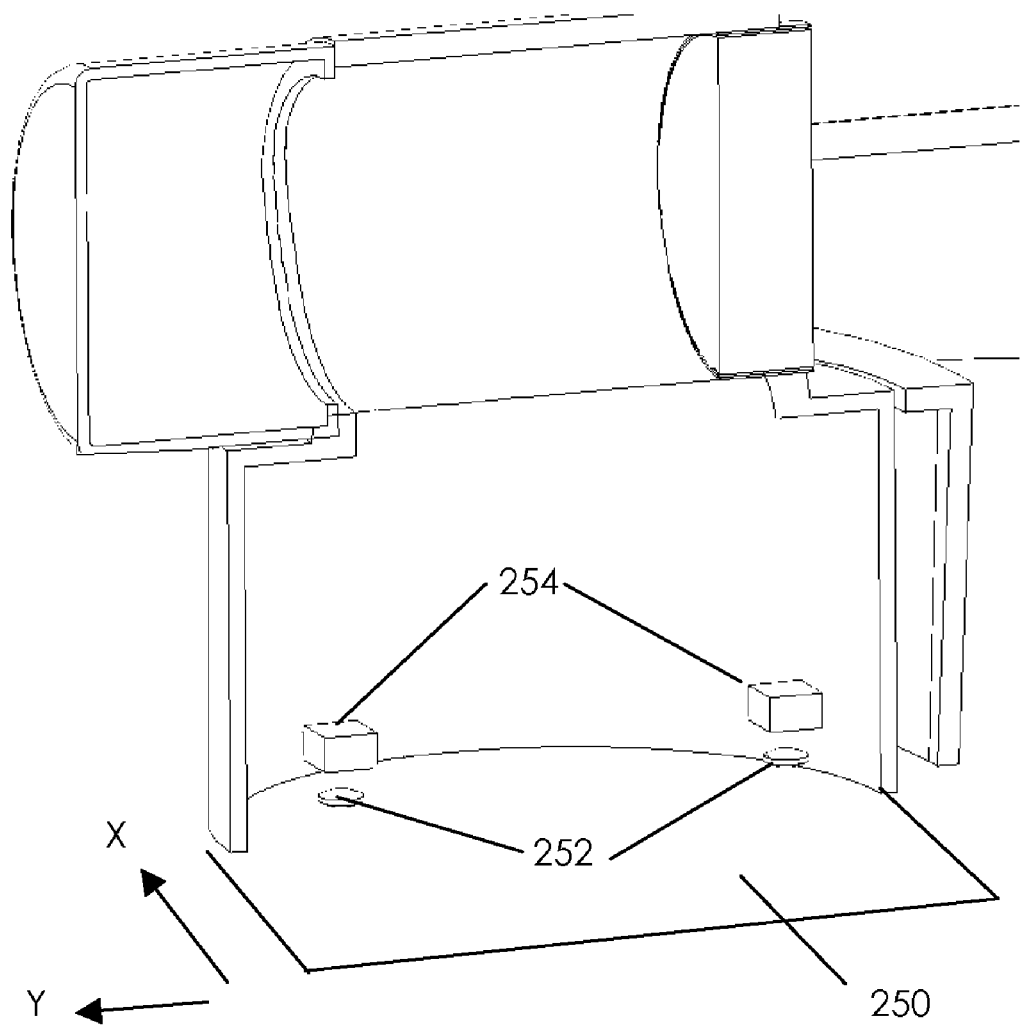
FIG. 7 shows an exemplary position determination system.

As detailed in FIG. 7, the planar encoder system measures the translational and angular position of the mobile scanner platform on the reference plate (the x, y and yaw axes). It includes the reference plate 140 and two small imagers 254 with two imaging lenses 252 affixed to the mobile scanner platform chassis in diametrically opposed positions. The reference plate 140 incorporates a pattern 250 into its upper layer that is imaged by these downward-looking sensors.

The upper layer 250 of the reference plate 140 may be composed of a sheet of dimensionally stable, optically clear material such as glass. On the underside of this layer a reference pattern may be photo-etched using a chrome-on-glass process. An appropriate pattern might be a 40 by 40 μm checkerboard to be imaged at 10 μm per pixel. For a 256×256 pixel area sensor, this would provide 64 edge pixels per row or column for 642 or 4096 edge pixels in either direction.

Figure 8:
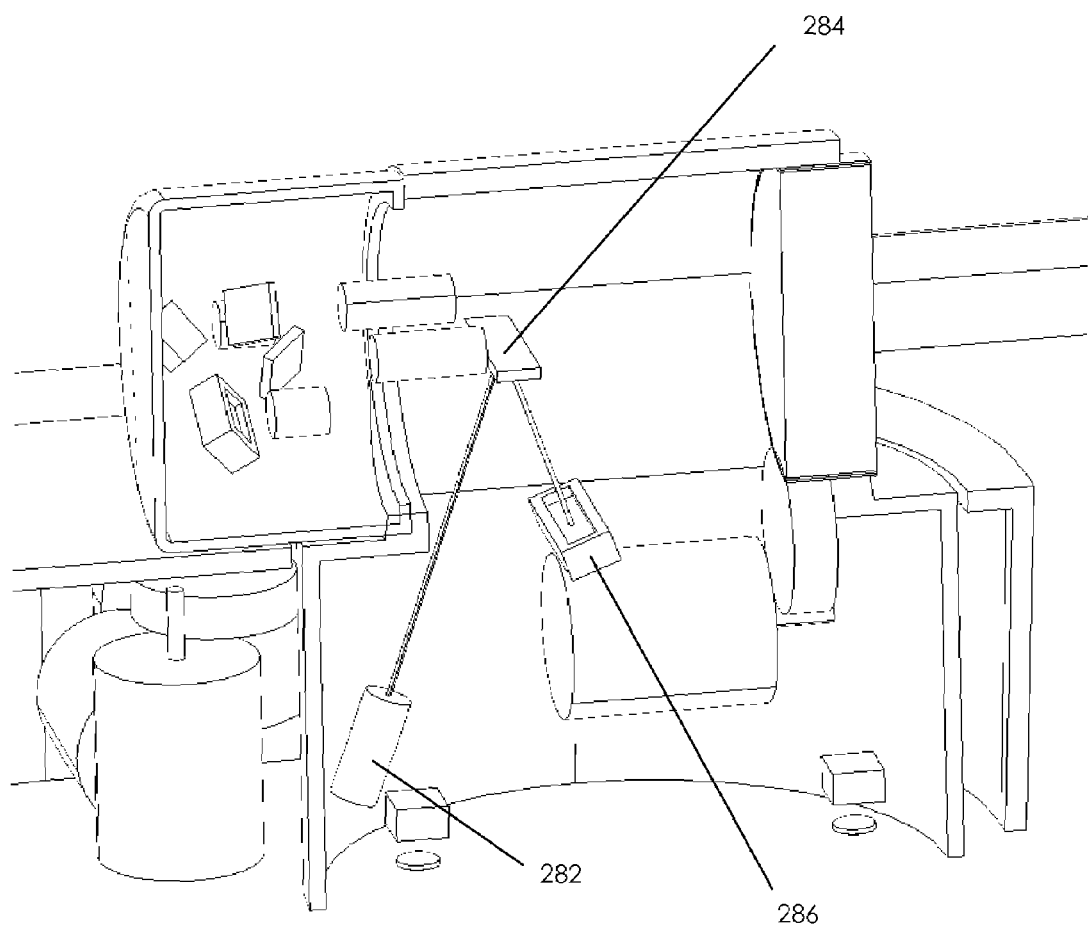
FIG. 8 shows the exemplary embodiment for determining roll and yaw.

The planar encoder measures position along three of the four degrees of freedom of the system, the remaining axis, the roll axis has a separate measurement system. In one implementation, the roll axis movements are achieved by two precision bearings mounted approximately 50 mm apart to allow for rotation of the scanner head probe 130 about the long axis of the scanner head holding arm 136. As shown in FIG. 8, the scanner head probe's angular roll position is measured by observing the deflection of a laser beam generated by a laser module 282 mounted to the mobile scanner platform chassis by a mirror 284 mounted to the rotating imaging assembly. Two mirrors are mounted to the assembly so that the angle may be measured when the scanner head probe is directed either maxillarily or mandibularly. The deflected beam is observed by a linear array sensor 286.

Two factors that influence the accuracy of the scanner include temperature and structural deformation. To eliminate temperature effects, the optical train itself is athermalized in one embodiment so that magnification and focus are invariant for the operating temperature range.

In another embodiment, since loading the system structurally during a scan may result in errors and must be avoided or detected, a tooth collision sensor or strain gauge is employed in the scanner head holding arm 136 to detect any untoward loadings.

In other embodiments, CCD cameras or imagers can be used based upon their higher sensitivity. Alternatively, CMOS imagers can be used with the following advantages: 1) no frame grabber is required; 2) frame rates of >1000 frames/sec; and 3) dynamic resizing of the image window is possible.

As discussed above, the intra-oral scanner 100 contains components that support one or more of the following functions: 1) illuminate the dental structure to be imaged; 2) digitally image a dental structure from different aspects; and 3) reposition both the illumination and imaging apertures so as to traverse the region of the intraoral cavity of interest. Further, the output of the intra-oral scanner 100 is received and processed as follows.

Figure 9:
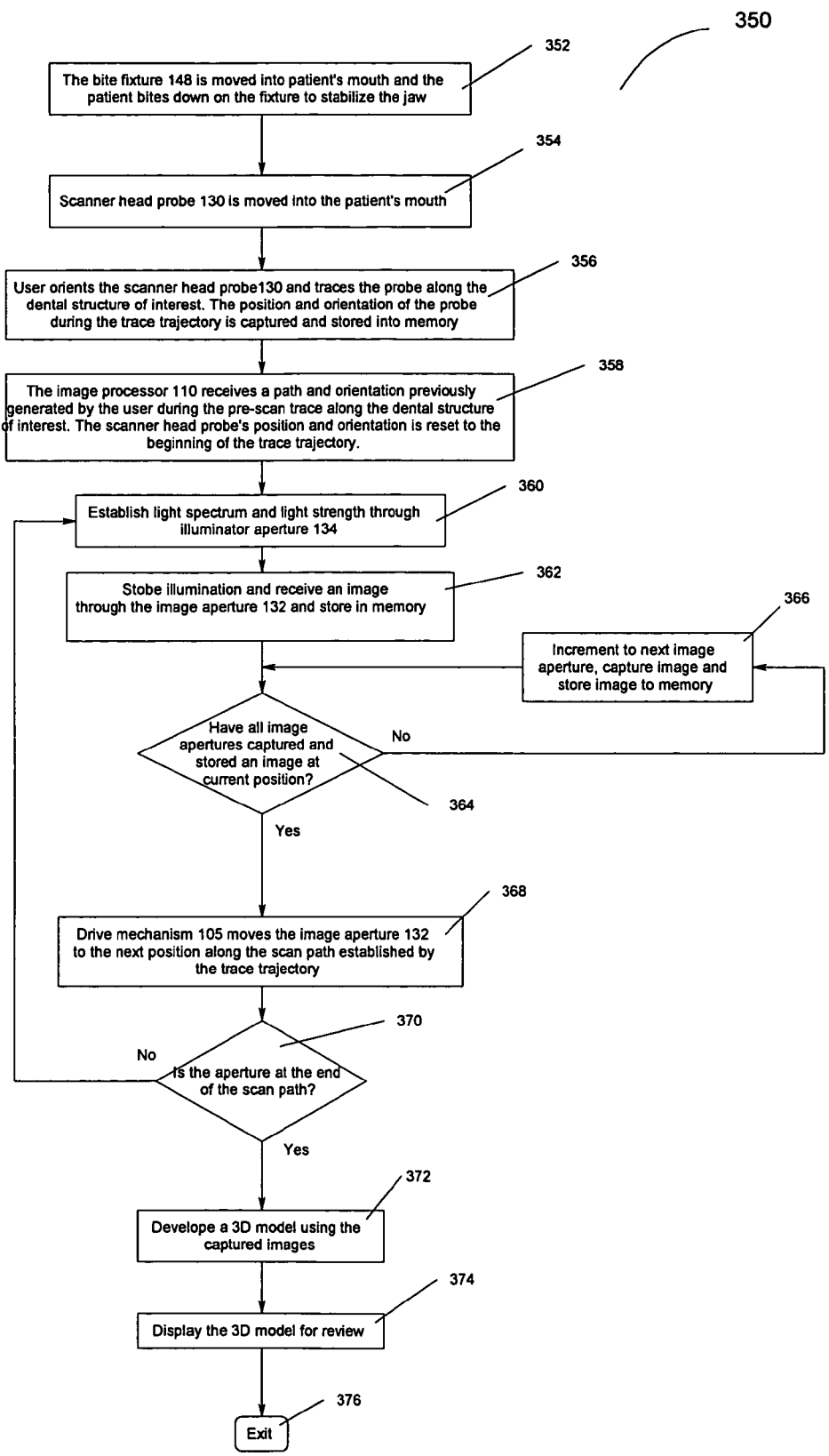
FIG. 9 shows an exemplary process for generating 3D models using the scanner of FIG. 1.

FIG. 9 shows an exemplary process 350 for scanning and generating 3D models of dental structures. First, the bite fixture 148 is moved into the patient's mouth and the patient bites down on the fixture to stabilize the jaw with respect to the reference plate 140 (step 352). Next, the scanner head probe 130 is moved into the patient's mouth (step 354). Next, the user orients the scanner head probe 130 with respect to the patient's dental structure of interest and traces the probe along a path covering the dental structure of interest. During the trace, the scanner system 100 measures and captures to memory the position and orientation of the scanner head probe 130 to create a trace trajectory (step 356). Next, a reset operation is performed to move the scanner head probe 130 to an initial known position at the beginning of the trace trajectory (step 358). The illuminator 134 position, light spectrum and light strength are established (step 360). The image processor receives an image through the image aperture 132 and captures the image to its memory (step 362). The image processor 110 then checks whether all image apertures have captured and stored an image at the current position along the trace trajectory (step 364). If more images are needed, the image processor 110 instructs each remaining image aperture 132 and illuminator aperture 134 to collect and store an image (step 366). The image processor 110 then actuates the drive mechanism 105 to move the scanner head probe 130 to the next incremental position and orientation along the trace trajectory (step 368). Next, the process 350 tests whether the scanner head probe 130 has reached the end of the trace trajectory (step 370). If not, the process loops back to step 360 to continue the image acquisition operation. If the end has been reached, the process 350 generates a 3D model using the captured images (step 372) and displays the 3D model for review (step 374). The process 350 then exits (step 376).

In another implementation, image-processing operations based on triangulation can be used where beams of light are projected onto the dental structures and three-dimensional spatial locations are determined for points where the light reflects from the dental structure object. As the reflected light bounces off the object at an angle relative to the known location and bearing of the light source, the system collects the reflection information from a known location relative to the light source and then determines the coordinates of the point or points of reflection by triangulation. A single dot system projects a single beam of light which, when reflected, produces a single dot of reflection. A scan line system beams a plane of light against the dental structure and which is reflected as a curvilinear-shaped set of points describing one contour line of the object. The location of each point in that curvilinear set of points can be determined by triangulation. The system projects a light plane (i.e., a laser stripe) from a known location and reads the reflection of multiple points depicting the contour of the dental structure at a location distant from the camera and from which the position can be triangulated.

In addition to optical triangulation systems, other alternative optical scanning systems can be used, including range meters systems. Range meter systems typically use an infrared-pulsed laser and mechanical scanning techniques to project a dot laser across an object and then measure the phase delay of the reflected signal. Once the dental structure coordinates have been scanned, the system removes redundant points and generates a 3D model from the scanned data using various techniques known in the art. In one embodiment, the process examines data for two adjacent laser stripes. Next, the process sweeps through each Y coordinate from the top of the two laser stripes to the bottom of the two stripes and creates triangles for the geometric 3D model. When the process has reached the bottom of the stripes, the triangulating process for the current laser stripes is finished and the next set of adjacent scan lines are retrieved until a triangulated mesh covering the whole dental structure is generated. Once the mesh has been generated, a 3D model with realistic shading and lighting can be generated.

In yet other embodiments, air nozzles are used for providing additional capabilities of directing pressurized air at the dental structure that is being imaged to 1) create a dry field; and 2) allow sub gingival image capture. Furthermore, these embodiments provide a spray orifice for dispensing a coating substance such as titanium dioxide or a luminescent compound onto the dental structures during the digital imaging process. The timing, duration and intensity of the directed air source and spray dispensing on the dental structure are precisely controllable. In one implementation, the pressurized air source is obtained by interfacing the apparatus to an existing air source using an industry standard interface at the patient dental chair.

At each lateral position, as the image aperture traverses an arc over the dental structure, the air jet output is directed at the region of the dental structure currently being imaged and is synchronized with the image capture. The spray orifice is also directed at the dental structure being imaged but dispenses the coating prior to image capture. Yet another embodiment uses multiple air jets to simultaneously direct air at multiple regions of the dental structure in synchronism with the capture of the dental structure images. In this embodiment a plurality of air jets are mounted in a known orientation to one another on a laterally moveable apparatus. The number of air jets and their orientation is selected to provide sufficient coverage and overlap of the dental structure to be digitally imaged and modeled. The pressurized air source may be integral to the mouthpiece or connected directly to the mouthpiece via tubing. In the latter case, the pressurized air source is ideally an existing source located at the patient dental chair. The mouthpiece would connect to this source using a standard industry interface.

In one embodiment, the air nozzle receives air from an air source through a flexible hose such as a rubber hose. The air supply is passed through an air regulator that is in turn connected to an air solenoid to turn on and off the air at appropriate time. A stream of air is directed at the surface of the dental structure using the nozzle. As the air is directed in a thin low pressure stream onto the dental structure, the particles may be dislodged from the surface of the dental structure while the dental structure is dried. The air flow or stream is preferably directed at the dental structure in a substantially fan-shaped or conical flow pattern so that air strikes the structure at a range of angles up to about 45 degrees with respect to the surface of the tooth. This conical flow pattern is elliptical in cross-section with a length as much as two to three times its width. In another embodiment for spraying materials such as whitening ingredients or a luminescent compound to the dental structure, air supplied by a compressor is delivered to a chamber in the nozzle. The compressed air in the chamber creates suction on a material line, which runs from the chamber to a tank containing the coating material. The suction draws material from the tank into the chamber and entrains the material with the compressed air for delivery onto the dental structure.

Next, a method for generating a three-dimensional model of a non-opaque structure is discussed. The method includes coating the structure with a luminescent substance to enhance the image quality, the luminescent substance having an excitation range; operating an illumination source at a frequency within the excitation range of the luminescent material; and capturing one or more images of the structure through at least one image aperture each having a frequency sensitivity, wherein the frequency sensitivity of each image aperture is maximized for the luminescent material emission range. A luminescent substance such as phycobiliproteins/phycobilisomes, among others, is used as an imaging enhancing coating applied onto the dental structures during the digital imaging process. As an alternative to spraying, the luminescent substance may be applied to the dental structures as a mouth rinse or as a brush-on or drench applied by the dentist just prior to imaging.

In addition, the model produced by the system described above can be automatically fused and displayed with other 3D images such as CT, MR or any other imaging that provides a 3D data set. Thus, if the patient's anatomy is known relative to a fixed reference, the model generated by the scanner system 100 can be displayed so that it automatically correlates with an imaging data base for display purposes.

It is to be understood that various terms employed in the description herein are interchangeable. Accordingly, the above description of the invention is illustrative and not limiting. Further modifications will be apparent to one of ordinary skill in the art in light of this disclosure.

The invention has been described in terms of specific examples which are illustrative only and are not to be construed as limiting. For example, although the buffer memory is described as high speed static random access memory (SRAM), the memory can be any suitable memory, including DRAM, EEPROMs, flash, and ferro-electric elements, for example. The invention may be implemented in digital electronic circuitry or in computer hardware, firmware, software, or in combinations of them.

Apparatus of the invention may be implemented in a computer program product tangibly embodied in a machine-readable storage device for execution by a computer processor; and method steps of the invention may be performed by a computer processor executing a program to perform functions of the invention by operating on input data and generating output. Suitable processors include, by way of example, both general and special purpose microprocessors. Storage devices suitable for tangibly embodying computer program instructions include all forms of non-volatile memory including, but not limited to: semiconductor memory devices such as EPROM, EEPROM, and flash devices; magnetic disks (fixed, floppy, and removable); other magnetic media such as tape; optical media such as CD-ROM disks; and magneto-optic devices. Any of the foregoing may be supplemented by, or incorporated in, specially-designed application-specific integrated circuits (ASICs) or suitably programmed field programmable gate arrays (FPGAs).

While the above embodiments have involved application of luminescent substances to dental structures, the invention is applicable to all non-opaque surfaces. Although an illustrative embodiment of the present invention, and various modifications thereof, have been described in detail herein with reference to the accompanying drawings, it is to be understood that the invention is not limited to this precise embodiment and the described modifications, and that various changes and further modifications may be effected therein by one skilled in the art without departing from the scope or spirit of the invention as defined in the appended claims.

What is claimed is:

1. A method for optically imaging a dental structure within an oral cavity, comprising:
   providing a reference plate having position fiducials marked thereon;
   providing a position sensor coupled to the reference plate to read the fiducials and determine position;
   moving a support arm inside the oral cavity, the support arm coupled to the reference plate providing a fixed coordinate reference frame external to the oral cavity, the support arm further having a scanner probe positioned on an intra-oral end;
   moving one or more image apertures on the arm;
   determining the position of the one or more image apertures using the fixed coordinate reference frame;
   capturing one or more images of the dental structure through one or more of the image apertures;
   generating a 3D model of the dental structure based on the captured images; and
   following a path and orientation previously generated by a user during a pre-scan trace with the one or more image apertures along the dental structure surface to be imaged.

2. The method of claim 1, comprising tracing a path with the one or more image apertures along the dental structure prior to capturing the images of the dental structure.

3. The method of claim 2, wherein the path is generated by a human operator.

4. The method of claim 1, comprising moving the one or more image apertures incrementally or continuously within the oral cavity.

5. The method of claim 1, comprising mounting one or more illuminator apertures to illuminate the dental structure.

6. The method of claim 1, comprising determining an intra-oral position and an orientation of the image aperture within the intra-oral cavity.

7. The method of claim 1, comprising measuring a holding arm position and orientation relative to a fixed coordinate reference frame.

8. The method of claim 7, wherein the fixed coordinate reference frame is defined by a coordinate reference frame reference plate.

9. The method of claim 1, comprising mounting a bite fixture to the reference plate.

10. The method of claim 9, comprising stabilizing patient jaws with the bite fixture during an image capture scan.

11. The method of claim 1, extending the one or more image apertures through a holding arm into the oral cavity.

12. The method of claim 1, comprising rotating the one or more image apertures about a holding arm axis to track the angular orientation of the teeth.

13. The method of claim 1, comprising rotating the one or more image apertures to image one or more of: maxillary teeth and mandibular teeth.

14. The method of claim 1, comprising adjusting a user-specified path to optimize the position and orientation of the image aperture with respect to the surface of the dental structure to be scanned.

15. The method of claim 14, comprising adjusting the image aperture to achieve one of the following: align the imaged dental structure in an aperture field of view; align the imaged dental structure in the image to an aperture depth of field; reduce image or illumination occlusion; and to alter the incident angle of the illumination on the surface.

16. The method of claim 1, comprising performing a stereometric analysis on the captured images.

17. The method of claim 1, wherein the 3D model generation includes performing structured light illumination and triangulation analysis on the captured images.

18. The method of claim 1, comprising displaying a representation of the 3D model and transmitting the 3D model over a network.

19. The method of claim 18, comprising using the 3D model for diagnosis and treatment of a patient.

* * * * *